United States Patent [19]

Beritashvili et al.

[11] Patent Number: 5,047,136
[45] Date of Patent: Sep. 10, 1991

[54] APPARATUS FOR ELECTROPHORETIC SEPARATION OF HIGH-MOLECULAR DNAS IN A GEL

[76] Inventors: David R. Beritashvili, ulitsa D. Ulyanova, 4, korpus 1, kv. 33; Lev V. Karklit, ulitsa Bolotnikovskaya, 38, korpus 5, kv. 2; Evgeny N. Tverdokhlebov, ulitsa Dnepropetrovskaya, 31, kv. 207, all of Moscow, U.S.S.R.

[21] Appl. No.: 423,453
[22] PCT Filed: Nov. 25, 1988
[86] PCT No.: PCT/SU88/00241
 § 371 Date: Oct. 2, 1989
 § 102(e) Date: Oct. 2, 1989
[87] PCT Pub. No.: WO89/07261
 PCT Pub. Date: Aug. 10, 1989

[30] Foreign Application Priority Data

Feb. 2, 1988 [SU] U.S.S.R. ................................ 4365904

[51] Int. Cl.⁵ ...................... B65D 85/18; B65D 75/00
[52] U.S. Cl. ............................ 204/299 R; 204/180.1; 204/182.8
[58] Field of Search ......................... 204/180.1, 299 R

[56] References Cited

U.S. PATENT DOCUMENTS 4,473,452 9/1984 Cantor et al. ............... 204/299 R X

OTHER PUBLICATIONS

Chu, Vollrath, Davis, Separation of Lg. DNA Molecules by Contour-Clamped Homogeneous Electric Fields, Science, vol. 234, 1986, pp. 1582-1585.

Primary Examiner—John F. Niebling
Assistant Examiner—Caroline Koestner
Attorney, Agent, or Firm—Burgess, Ryan & Wayne

[57] ABSTRACT

The apparatus comprises electrophoresis chamber (1) with positioned therein along the sides of a rectangle electrode groups (2,3,4,5) of equidistantly positioned electrodes. One pair of subtending electrode groups (2,4) is connected to power supply (8), the other pair of subtending electrode groups (3,5) is connected to power supply (10) via switch (9).

2 Claims, 2 Drawing Sheets

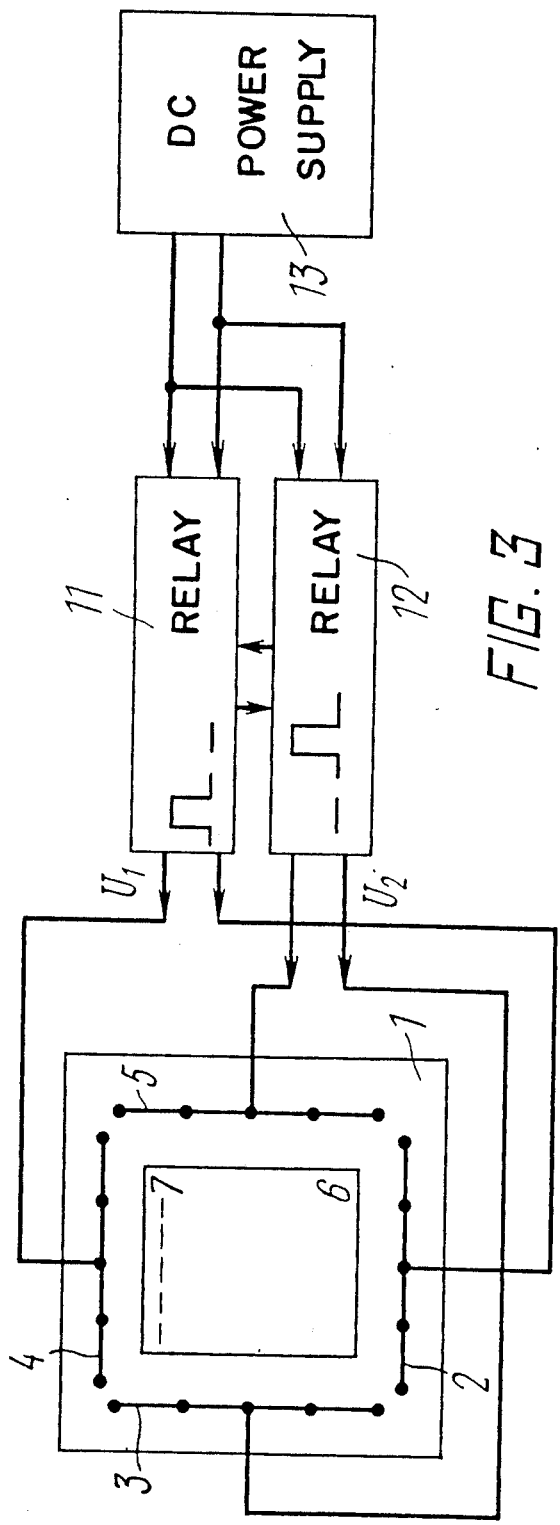
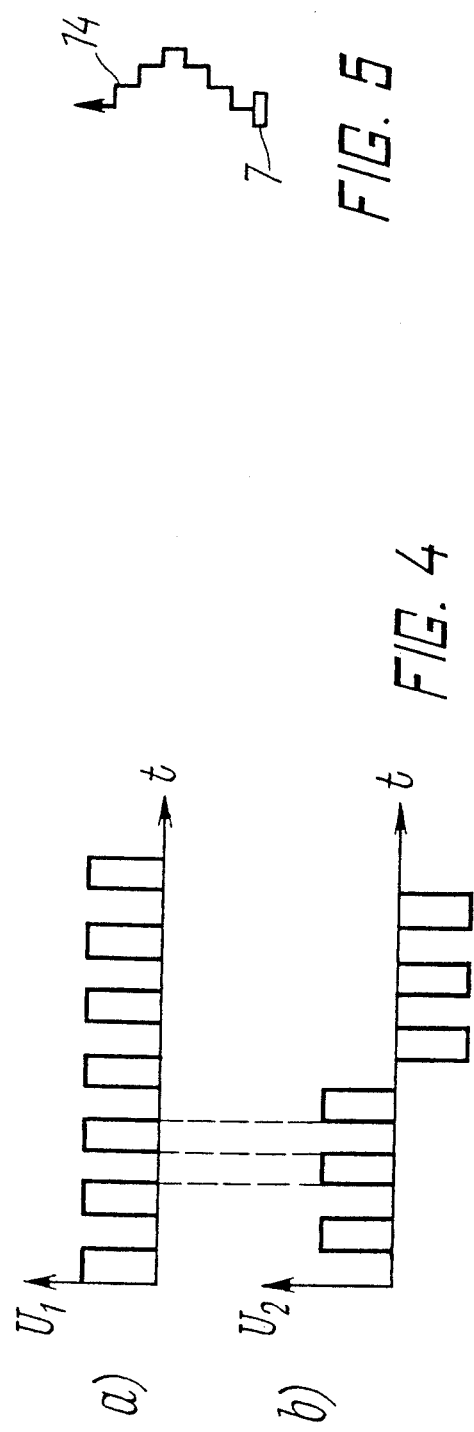

APPARATUS FOR ELECTROPHORETIC SEPARATION OF HIGH-MOLECULAR DNAS IN A GEL

FIELD OF THE INVENTION

This invention relates to the area of electrophoretic separation and analysis of biopolymers, and more specifically to apparatuses for electrophoretic separation of molecular weight DNA in a gel.

PRIOR ART

Separation of mixtures of biopolymers, in particular those whose size exceeds $5.10^4$ pairs of nucleic bases, is based on pulse electrophoresis, comprising successive generation of crossed electric fields in the gel with the mixture of molecular weigh DNA.

Known in the art is an apparatus for separating a mixture of DNA molecules (G. F. Carle, M. Frank and M. V. Olson. Electrophoretic Separation of Large DNA Molecules by Periodic Inversion of the Electric Field.—Science, v. 232, 1986, pp. 65-68), wherein the rectangular electrophoresis chamber is fitted with two opposite linear electrodes positioned horizontally, between which the gel unit is placed. The voltage from a power supply is applied to the electrodes via a switch, so that during $\frac{3}{4}$ of the time interval selected the electrodes are under a direct voltage and $\frac{1}{4}$ of this time interval—under a reverse voltage, this cycle repeated many times. This causes the direction of DNA molecule movement to vary periodically by 180°. Such an angle is not optimal for a wide range of molecular masses of DNA molecules being separated and consequently individual fractions with size above $2.10^6$ nucleic base pairs (NBP) cannot be separated in this known apparatus. Furthermore, reciprocal movement of the molecules in the gel unit results in a longer time to separate the initial mixture, i.e. to lower productivity of the apparatus.

Also known in the art is an apparatus (G. Chy, D. Vollrath, R. W. Davis, Separation of Large DNA Molecules by Contour=Clamped Homogeneous Electric Fields, Science, v. 234, 1986, pp. 1582-1585), wherein six groups of point electrodes, positioned vertically relative to the gel unit, form a hexahedron, electrically looped via identical resistors, enclosing the gel unit. The voltage from a power supply is alternately applied via a switch to two pairs of oppositely positioned electrode groups. A third pair of electrodes is passive and serves to generate a uniform electric field between electrodes. In this arrangement DNA molecules move with a change in direction by 120° each voltage switching clock interval. At the same chamber size as in the previously cited apparatus, the gel unit has to be smaller and consequently carry a smaller number of deposited samples, this is also impaiiring the productivity of the apparatus. Furthermore, the power of the power supply has to be doubled because the current through the electrodes has to be not lower than through the buffer solution coating the gel unit.

Known in the art is an apparatus for separating high molecular weight DNA in a gel (U.S. Pat. No. 4,473,452) allowing separation of DNA molecules with sized ranging from $5.10^4$ to $9.10^6$ NBP. Its square electrophoretic chamber is fitted with four groups of electrodes, with two adjacent chamber walls mounting groups of point electrodes electrically connected to each other within a group, and the other two adjacent walls mounting two individual point electrodes in the immediate vicinity from the ends of two opposite to them electrode groups. The voltage from a power supply is applied via a switch to the electrodes, with voltage of negative polarity applied to the group of electrodes and with voltage of positive polarity applied to the opposing individual electrode for a certain time interval, then the voltage is switched to the second group of electrodes and second individual electrode for the same time interval and in the same polarity arrangement. This causes crossed curvilinear electric fields in the gel unit positioned inside this chamber, causing DNA molecules to move along complex paths, the direction whereof varies from 90° to 180° as the molecule approaches the point electrodes.

Curvature of the fields generated in this known apparatus results, firstly, in curvilear tracks of individual DNA fraction movement in the gel, this highly complicates the problem of determining their molecular masses and requiring the use of special conrrection programs for automatic processing of the results, for instance, when using gel scanners. Secondly, the number of simultaneously separated DNA molecule samples is rather small, because the extreme tracks may due to curvature leave the gel and enter the buffer solution.

Known in the art is an apparatus for electrophoretic separation of high molecular weight DNA in a gel (PCT SU, 88/00124), comprising an electrophoretic chamber with four identical groups of electrodes spaced equidistantly within each group and interconnected with the aid of diodes. Electrode groups are positioned along the sides of an equilateral quadrangle (square, rhombus) and connected to a power supply via a switch. One pair of opposite electrode groups is connected to one output of this switch, the other pair to the other output of the switch, the input whereof is connected to the power supply.

When the power supply is turned on, one group of electrodes of a pair is fed a positive voltage and the other group of this pair is fed a voltage of negative polarity. DNA molecules are lined up along the electric field lines of force and begin moving toward the electrode group under positive potential. After a specified time interval the switch transfers the voltage to the other pair of electrode groups and DNA molecules arrange themselves along lines in force of a new direction and begin moving toward the positively charged group of electrodes. Thereafter the voltage is again switched back to the first group of electrodes and applied in the same polarity as during the first time period. After the same time interval, the voltage is again applied to the second group of electrodes, but with a polarity, reversed relative to that in the second time period. These four time periods constitute a cycle, which is repeated until the lightest DNA fractions do not arrive at a site opposite to the deposition side of the gel unit.

However, this known in art apparatus does not allow effective separation of individual DNA fractions with sizes above $2.10^6$ NBP.

DISCLOSURE OF THE INVENTION

This invention solves the problem of providing an apparatus for electrophoretic separation of high molecular weight DNA in a gel with a voltage supply circuit arrangement allowing generation of a uniform electric field along the entire cross-section of the gel unit, with the possibility of varying the field direction in the range from 90° to 180° during the process of separation of the initial mixture of DNA molecules.

This is achieved by and apparatus for electrophoretic separation of high molecular weight DNA in a gel, comprising an electrophoresis chamber of rectangular shape with four identical groups of electrodes positioned at the rectangle sides and enclosing a gel unit, with electrodes equidistantly positioned within each group, a switch and a power supply, according to the invention is further complemented with a supplementary power supply, wherein one pair of subtending electrode groups is connected to the outputs of the switch, the inputs whereof are connected to the outputs of the supplementary power supply, and the other pair of subtending electrode groups is connected to the outputs of the main power supply.

This is also achieved by an apparatus for electrophoretic separation of high molecular weight DNA in a gel, comprising an electrophoresis chamber with four identical electrode groups positioned along the sides of a rectangle and enclosing the gel unit, with electrodes positioned equidistantly within each group, a switch and a power supply, according to this invention is further complemented with a supplementary switch connected to the outputs of the power supply and to the main switch, the inputs whereof are connected to the outputs of the power supply, wherein one pair of subtending electrode groups is connected to the power supply via the main switch and the other pair of subtending electrode groups is connected to the power supply via the supplementary switch.

The invention allows an improved productivity of the process of DNA molecule mixture separation.

BRIEF DESCRIPTION OF ACCOMPANYING DRAWINGS

These and other objectives and advantages of the invention will become apparent from the following description thereof with reference to specific embodiments thereof and to the accompanying drawings, wherein:

FIG. 3 shows the block diagram of a second embodiment of the apparatus for electrophoretic separation of high molecular weight DNA in a gel, according to the invention;

FIG. 4 shows the time diagram of voltages applied to electrode groups of the second embodiment of the apparatus, according to the invention;

FIG. 5 shows DNA molecule movement paths in a gel, according to the invention.

PREFERRED EMBODIMENTS OF THE INVENTION

Figure 1:
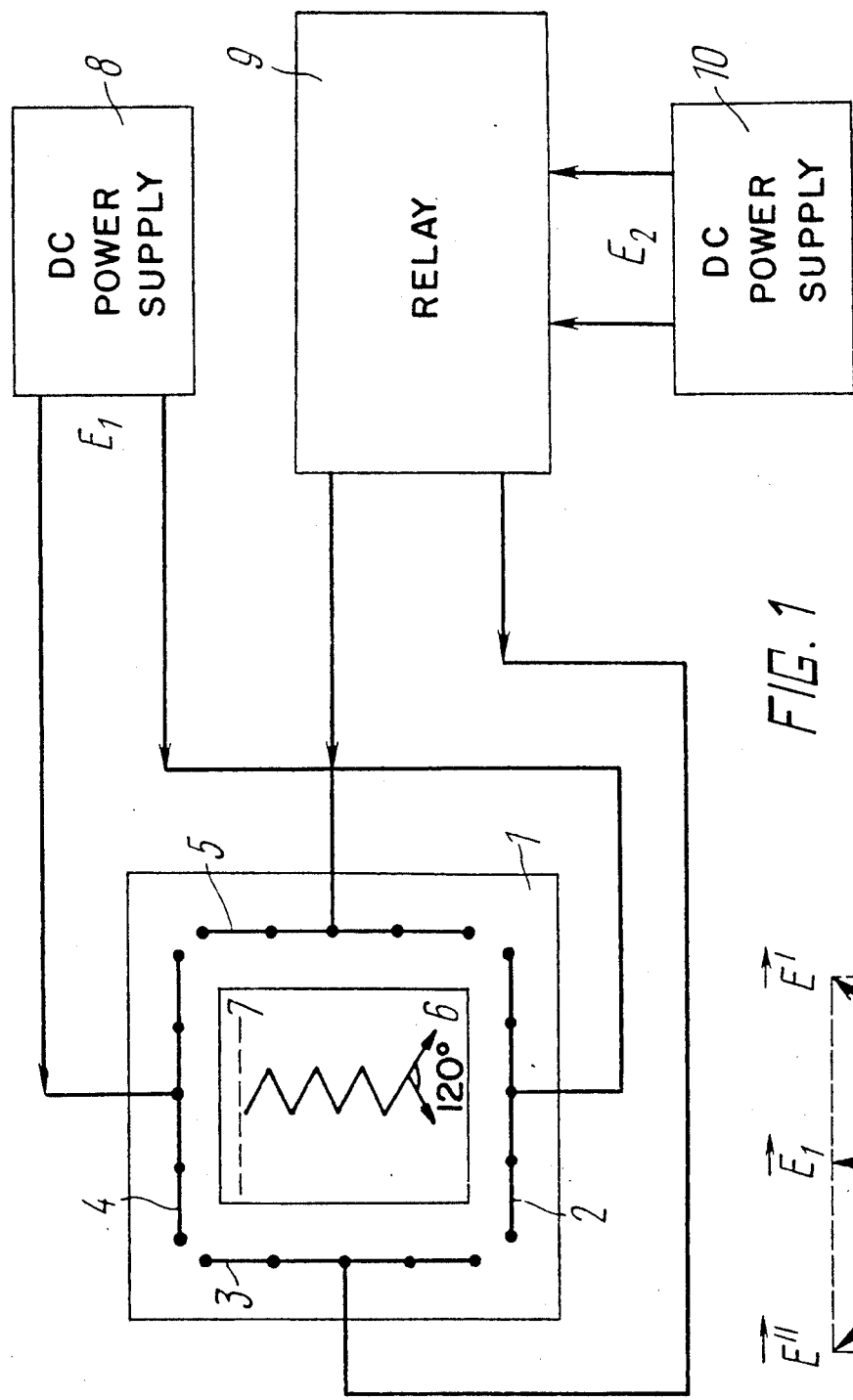
FIG. 1 shows the block diagram of the first embodiment of the apparatus for electrophoretic separation of high molecular weight DNA in a gel, according to the invention.

The apparatus for electrophoretic separation of high molecular weight DNA in a gel comprises electrophoresis chamber 1 (FIG. 1) of rectangular shape with four identical electrode groups 2, 3, 4, 5, each comprising an equal number of electrodes interconnected via diodes (not shown in the Figure). Electrode groups 2, 3, 4, 5 are mounted on a holder (not shown in the Figure), simultaneously serving as the top cover of electrophoresis chamber 1, along the sides of a rectangle enclosing positioned on the chamber 1 bottom gel unit 6 with one side thereof carrying samples 7 of DNA molecule mixtures. Gel unit 6 is bathed in a buffer solution providing current passage between appropriate electrode groups 2, 3, 4, 5, when voltage is applied to them. Electrode groups 2, 4 are connected to power supply 8, groups 3, 5—to power supply 10 via switch 9.

Figure 2:
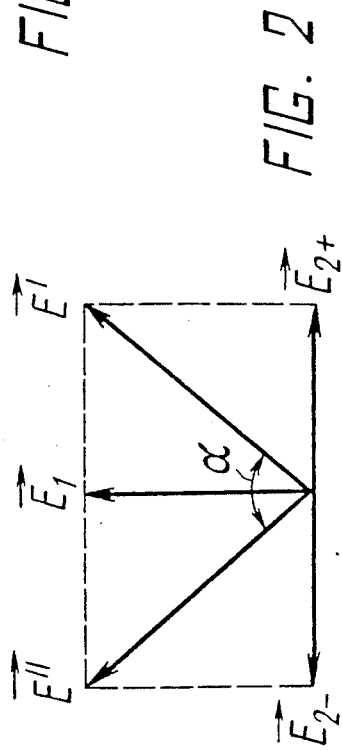
FIG. 2 shows a vector diagram of voltages defining the paths of DNA molecules movement in a gel unit, according to the invention.

FIG. 2 shows the vector diagram of electric field intensity which defines the path of DNA molecule movement; here $\overline{E}_1$ is the electric field intensity generated between electrode groups 2 and 4 (FIG. 1) at enabled power supply 8; $\overline{E}_{2+}$ (FIG. 2) is the vector of electric field intensity generated between electrode groups 3 and 5 (FIG. 1) with voltage of one polarity applied from power supply 10; $\overline{E}_{2-}$ (FIG. 2) is the vector of electric field intensity generated between electrode groups 3 and 5 (FIG. 1) at an opposite voltage polarity; $\overline{E}'$ (FIG. 2) is the resulting field intensity vector, $\overline{E}' = \overline{E}_1 + \overline{E}_{2+}$; $\overline{E}''$ is resulting field intensity vector at an opposite voltage polarity, $\overline{E}'' = \overline{E}_1 + \overline{E}'_{2-}$; and $a$ is the angle between vectors $\overline{E}'$ and $\overline{E}''$.

In the second embodiment of the apparatus electrode groups 2 and 4 (FIG. 3) are connected to the outputs of switch 11 and electrode groups 3 and 5 are connected to the outputs of switch 12, with the inputs of switches 11 and 12 interconnected and connected to the outputs of power supply 13.

FIG. 4 shows voltage pulses $U_1$ and $U_2$ arriving from power supply 13 (FIG. 3) at electrode groups 2, 4 and 3,5, respectively.

FIG. 5 shows DNA molecule movement path from sample 7 in gel unit 6 (FIGS. 1,3).

The apparatus for electrophoretic separation of high molecular weight DNA in a gel of the invention functions as follows. Gel unit 6 with applied samples 7 (FIG. 1) of DNA molecule mixture is positioned in electrophoresis chamber 1 paralled to its walls and flooded with a buffer solution contacting the electrodes of all four electrode groups 2, 3, 4, 5. Voltage from power supply 8 is applied to electrode groups 2 and 4, with a voltage of arbitrary polarity passed to electrode groups 3 and 5 from power supply 10 via switch 9. This results in DNA molecules being affected by two electric fields: an electric field with an intensity $\overline{E}_1$ (FIG. 2) generated between electrode groups 2 and 4 (FIG. 1) on turning on power supply 8 and an electric field with an intensity $\overline{E}_{2+}$ (FIG. 2) generated between electrode groups 3 and 5 by the voltage from power supply 10. The direction of DNA molecule movement is defined by vector $\overline{E}'$ (FIG. 2), which is the vector sum of $\overline{E}_1$ and $\overline{E}_{2+}$. After a specified time interval, switch 9 (FIG. 1) reverses the polarity of the voltage applied of electrode groups 3 and 5, this causing DNA molecules to change the direction of their movement by an angle equal to $a$ (FIG. 2), where $\mathrm{tg}\, a/2 = \overline{E}_{2-}/\overline{E}_1$ because $\overline{E}'$ becomes $\overline{E}' = \overline{E}_1 + \overline{E}_{2-} + \overline{E}_{2-}$.

Consequently, fixed values of voltages from power supplies 8 and 10 (FIG. 1) uniquely define the angle $a$ (FIG. 2) by which DNA molecule movement paths are changed during initial mixture 7 separating. Variation of one or both voltages allows control of angle $a$ (FIG. 2) during the separation process in the range $90° \leq a \leq 180°$, i.e. by providing a supplementary power supply 10 (FIG. 1) and simultaneous connection of both power supplies 8 and 10 to appropriate electrode groups a superposition of uniform electric fields is produced at the site of gel unit 6 location in the apparatus.

Effective separation of long chain DNA molecules with sizes approaching the method's resolution ($5.10^6$ to $10^7$ NBP) electrophoresis of several day durations are used with electric field intensities 4 to 5 times lower than usual. To avoid premature depletion of the buffer solution it is expedient to employ a different supply arrangement, wherein the voltage to subtending electrode groups 2,4 and 3,5 (FIG. 3) is applied alternately. This in acomplished by using a supplementary switch 13 (FIG. 3) In this case pulses $U_1$ (FIG. 4a) from power supply 13 (FIG. 3) are applied to electrode groups 2 and 4 via switch 11, these pulses being of one polarity and of a 0.5 duty factor. In pauses between $U_1$ pulses, pulses $U_2$ (FIG. 4b) of arbitrary polarity are passed by switch 12 (FIG. 3) to electrode groups 3 and 5 during half the time specified. Thereafter the polarity of $U_2$ pulses at electrode groups 3 and 5 (FIG. 3) is reversed, this reversal of polarity being performed during the entire period of initial DNA molecule mixture separation; the corresponding paths of molecule movement are shown in FIG. 5. Using this circuit arrangement to separate DNA of smaller sizes does not affect the resolution, but the separation time is $2\frac{1}{2}$ times longer.

Thus, complementing the apparatus with a supplementary power supply 10 (FIG. 1) or supplementary switch 12 (FIG. 3) improves the productivity of the apparatus and expands the range of separable by molecular mass DNA molecules. In both embodiments separation of high molecular weight DNA molecules in a gel is achieved with the aid of electrode groups 2, 3, 4, 5 (FIGS. 1,3) positioned along the sides of a rectangle, with equidistant arrangement of electrodes in groups 2, 3, 4, 5 and connected in parallel or series to power supplies 8, 10 (FIG. 1) and 13 (FIG. 3) to generate a sequence or superposition of uniform electric fields providing a specified angle $\alpha$ (FIG. 2) of variation of the direction of DNA molecule movement in gel unit 6 (FIGS. 1,3). This ensures complete usage of the total surface of gel nit 6 and allows programmable variation of the conditions of DNA molecules separation in experiments.

INDUSTRIAL APPLICABILITY

The invention can be successfully used in bioengineering, molecular biology and genetics, biochemistry, and also in medicine and agriculture.

We claim:

1. An apparatus for electrophoretic separation of high molecular weight DNA in a gel, comprising a rectangular electrophoresis chamber having a gel unit therein positioned along the sides thereof, four identical groups of equidistant positioned electrodes, a main power supply, a supplemental power supply and a switch having one subtending pair of said electrode groups connected to the output of the switch, and the input of the switch connected to the output of the supplementary power supply, and the other subtending pair of said electrode groups connected to the output of the main power supply.

2. An apparatus for the electrophoretic separation of high molecular weight DNA in a gel, comprising a rectangular electrophoresis chamber having a gel unit therein positioned along the sides thereof, four identical groups of equidistant positioned electrodes, a main power supply, a main switch, and a supplemental switch said supplemental switch connected to the output of the main power supply and to the main switch, the input of the main switch connected to the output of the main power supply with one subtending pair of electrode groups connected to the main power supply via the main switch and the other subtending pair of electrode groups connected to the power supply via the supplementary switch.

* * * * *